United States Patent [19]
Wong et al.

[11] Patent Number: 5,968,548
[45] Date of Patent: Oct. 19, 1999

[54] USE OF LIPOSOME ENCAPSULATED CIRPROFLOXACIN AS AN IMMUNOTHERAPEUTIC DRUG

[75] Inventors: Jonathan P. Wong, Medicine Hat, Canada; Edward G. Saravolac, Bath, United Kingdom; Les P. Nagata, Medicine Hat, Canada

[73] Assignee: Minister of National Defence of Her Majesty's Canadian Government, Ottawa, Canada

[21] Appl. No.: 08/843,589

[22] Filed: Apr. 16, 1997

[30] Foreign Application Priority Data

Apr. 23, 1996 [CA] Canada ................................... 2174803

[51] Int. Cl.$^6$ ..................... A61K 91/127; A61K 31/47; A01N 43/42
[52] U.S. Cl. ................ 424/450; 424/85.1; 424/234.1; 424/831; 514/312; 514/311; 514/313; 514/314
[58] Field of Search ................ 514/712, 312, 514/912, 311, 313, 314; 424/450, 184.1, 85.1, 234.1, 831; 436/829; 568/29, 41

[56] References Cited

U.S. PATENT DOCUMENTS

| | | | |
|---|---|---|---|
| 4,692,454 | 9/1987 | Mich et al. | 514/312 |
| 4,923,699 | 5/1990 | Kaufman | 424/427 |
| 5,108,921 | 4/1992 | Low et al. | 435/240.1 |
| 5,643,599 | 7/1997 | Lee et al. | 424/450 |

FOREIGN PATENT DOCUMENTS

| | | |
|---|---|---|
| 0 317 120 | 5/1989 | European Pat. Off. . |
| 2 002 319 | 2/1979 | United Kingdom . |
| 91/09616 | 7/1991 | WIPO . |

OTHER PUBLICATIONS

"Liposome–entrapped Ampicillin in the Treatment of Experimental Murine Listeriosis and Salmonellosis" by E. Fattal et al Antimicrob. Agents Chemother, 35 pp. 770–772, 1991.

Liposome–mediated Treatment of Viral, Bacterial, and Protozoal Infections Popescu et al Liposomes: from Biophysics to therapeutics, In. M. J. Ostro (ed.), Marcel Dekker, Inc. pp. 219–251, 1987.

"Pharmokinetics and in vivo Activity of Liposome Encapsulated Gentamicin" by C. E. Swenson et al Antimicrob. Agents Chemother, 34 pp. 235–240, 1990.

Cells Mater. 3 (3) p. 321 (1993) Abstract only Nicholov.

Antimicrob Agents Chemother. 36 (12) p. 2808 (1992) Abstract only Majumdar.

Zhang et al. "Necessity and sufficiency of beta interferon for nitric oxide production in mouse peritoneal macrophages". infection and Immunity. vol. 62, No. 1, pp. 33–40, Jan. 1994.

*Primary Examiner*—Lynette F. Smith
*Assistant Examiner*—Datquan Lee
*Attorney, Agent, or Firm*—Nixon & Vanderhye, P.C.

[57] ABSTRACT

Liposome-encapsulated quinolones and specifically liposome-encapsulated ciprofloxacin dramatically enhances macrophage functions, induces NO production and augments the production of cytokines, rendering the composition an immunoprophylactic and immunotherapeutic agent with unique clinical potential. Liposome-encapsulated ciprofloxacin and other quinolones could be extremely useful in antimicrobial, anticancer and AIDS therapies. In such cases, the immunological status of the patient is often compromised or suppressed, making them susceptible to microbial infections and to the development of tumor growth. Selective augmentation of cellular immunity by activation of the microbicidal and tumoricidal activities of macrophages, induction of NO and cytokine production could be of primary importance to such patients in terms of protecting them against microbial infections and inducing their cellular host defense to tumor cells.

2 Claims, 5 Drawing Sheets

USE OF LIPOSOME ENCAPSULATED CIRPROFLOXACIN AS AN IMMUNOTHERAPEUTIC DRUG

This invention relates to an immunoprophylactic and immunotherapeutic drug composition, and a process for using such composition.

BACKGROUND OF THE INVENTION

More specifically, the invention relates a liposome-encapsulated ciprofloxacin, and to the use of such composition for stimulate host cell-mediated immunity to resist microbial infections and to enhance macrophage killing of microbial pathogens and cancer cells.

The present inventor has already proposed use of liposome-encapsulated ciprofloxacin as an antibiotic (see Canadian Patent Application Serial No. 2,101,241, filed Jul. 23, 1993). Further research by the inventor has a liposome-encapsulated quinolone, specifically ciprofloxacin can be used as an immunoprophylactic and immunotherapeutic agent.

Chronic bacterial, viral and fungal infections, as well as a number of neoplastic diseases can cause significant impairment to a host's immune defense system ability to fight diseases (D. A. Cooper et at, "Characterization of T lymphocyte responses during primary infection with human immunodeficiency virus", 1988, J. Infect. Dis. 157:889–896" and A. Sher et al, "Role of T-cell derived cytokines in the downregulaton of immune responses in parasitic and retroviral infection", 1992, Immunol. Rev. 127:183–204). In cancer patients undergoing chemo-and/or radiation therapy, the immune system is usually further suppressed, rendering them susceptible to infections. Some antibiotics currently used to prevent infections in immuno comprised individuals are themselves known to cause further suppression of the cellular and humoral immune responses (L. Bassie et al, "Conditions for immunosuppression by rafampicin", 1993, J. Infect. Dis. 128:736–744, T. E. Miller et al, "Clinical infections, antibiotics and immunosuppression: A puzzling relationship", 1981, The Amer. J. Med. 71:334–336 and W. E. Hauser et al, "Effect of antibiotics on the immune response", 1982, The Amer. J. Med. 72:711–716).

Attempts to elevate the host immune defense using immunotherapy with agents such as exogenous cytokines have become increasingly important in clinical applications in recent years, particularly for the immune therapy of AIDS, other immune deficiency disorders and cancer. However, such exogenous cytokines, including interleukins, interferons and tumor necrosis factors are known to cause serious toxic side effects (J. R. Quesada et al, "Clinical toxicity of interferons in cancer patients: a review", 1986, J. Clin. Oncol. 4:234–243 and C. A. Dinarello, "Role of interleukin-1 in infectious diseases", 1992, Immunol. Rev. 127:119–146). Moreover, the cytokines are expensive, and are rapidly cleared from the general circulation following systemic administration (B. A. Beutler et al, "Cachectin/tumor necrosis factors: production, distribution, and metabolic fate in vivo", 1985, J. Immunol. 135:3972–3977).

SUMMARY OF THE INVENTION

The object of the present invention is to provide a solution to the problems outlined above in the form of a liposome encapsulated quinolone, specifically ciprofloxacin for augmenting the ability of the host immune system to resist infections and to enhance the ability of macrophages to kill microbial pathogens and tumor cells.

According to one aspect, the present invention provides a composition for resisting infection and enhancing macrophage function comprising a liposome-encapsulated quinoline.

The therapeutic advantages of the use of the above described composition are that liposomes and/or ciprofloxacin are non-toxic relative to exogenous cytokines and are safe for human administration. Moreover, because therapeutic agents encapsulated in liposomes are released in a gradual and sustained manner, the immunomodulating effect provided by the agents are prolonged significantly in the body, enhancing their therapeutic effectiveness. In contrast, cytokines used in conventional immunotherapy are generally small proteins and peptides which are rapidly cleared from and/or metabolized in the body, leading to transient therapeutic effects. Such therapeutic advantages make liposome-encapsulated ciprofloxacin a safer, more effective and less expensive approach for immunotherapy. The present inventors have established that liposome-encapsulated ciprofloxacin can significantly enhance macrophage functions, induce the production of therapeutic cytokines, and elevate the production of nitric oxide (NO).

DETAILED DESCRIPTION OF THE INVENTION

CHEMICALS

Phosphatidylcholine, phosphatidylserine and cholesterol used in the preparation of liposomes were purchased from Avanti Polar Lipids (Alabaster, Ala.). Ciprofloxacin was acquired from Miles Canada Ltd. (Mississauga, Ont.). $^{14}$C-ciprofloxacin was obtained from Bayer Drug Company (Wuppertal, Germany). Lucigenin and zymosan A were purchased from Sigma Chemical Company (St. Louis, Mo.). Primers for cDNA for polymerase chain reaction (PCR) were purchased from (Clontech, Palo Alto, Calif.).

ANIMALS

The mice used in experimentation for the present invention were female BALB/c and CD1 mice purchased from Charles River Ltd. (St. Constant, Quebec). The animals were placed in quarantine in the vivarium for one week upon arrival, and were housed and cared for in a manner consistent with the guidelines set by the Canadian Council on Animal Care.

LIPOSOME PREPARATION

All liposomes used for the encapsulation of ciprofloxacin were prepared by the reverse-phase evaporation method (F. Szoka et al, "Procedure for preparation of liposomes with Large internal aqueous space and high capture by reverse-phase evaporations", 1978, Proc. Natl. Acad. Sci. USA. 75:4194–4198). The liposomes were prepared from phosphatidylcholine: cholesterol at a molar ratio of 7:3. To determine the amount of ciprofloxacin encapsulated within liposomes, $^{14}$C-ciprofloxacin was used as a radioactive tracer. Encapsulated radiolabelled ciprofloxacin was separated from unencapsulated material by ultracentrifugation at 125,000×g for 30 minutes. Entrapment efficiency was determined as a percentage ratio of radioactivity associated with the liposome pellet following ultracentrifugation step to the total radioactivity added to the lipid mixture.

TREATMENT OF MICE WITH LIPOSOME-ENCAPSULATED CIPROFLOXACIN

Groups of 5 mice were injected by the intraperitoneal route with free unencapsulated ciprofloxacin (1 mg/mouse), liposome-encapsulated ciprofloxacin (1 mg in 1 μmole equivalent lipid of liposomes), sham liposomes (1 μmole lipid equivalent) and PBS. At 48 hours following three daily doses, the mice were sacrificed by cervical dislocation, and the resident macrophages were isolated from the peritoneum cavity by harvesting with three washes of 5 ml Hanks balanced salt solution (HBSS, Flow Lab., Mississauga, Ont.). The macrophages were then purified using a Histopaque 1083 column (Sigma Chemical Co.).

MEASUREMENT OF PHAGOCYTIC ACTIVITY BY CHEMILUMINESCENCE ASSAY

Following purification by the Histopaque column, peritoneal macrophages were centrifuged at 3000 rpm for 15 min. The resultant cell pellet was then resuspended in 1 ml HBSS buffer. A 10 µl aliquot of the cell suspension was then used for cell counting by the tryphan blue dye exclusion method. The cell concentration of remaining cell suspension was then adjusted to $1 \times 10^7$ cells per ml of HBSS buffer. The chemiluminescence assay for the macrophages was performed in a black flat-bottom 96-well titertek fluoroplate (ICN Biomedicals, Inc. Horsham, Pa.). For each assay, 100 µl of freshly prepared $10^{-4}$M lucigenin in HBSS buffer was added to each well. Macrophage suspensions from different test and control groups were then added to the appropriate wells (50 µl per well, $1 \times 10^7$ cells per ml). The microtiter plate was loaded into the Titertek Luminoskan luminometer (Flow Laboratories, Mississauga, Ont.) with temperature control set at 37° C. After incubation for 10 min. inside the luminometer, opsonized zymosan particles (50 µl, $1 \times 10^8$ particles per ml of PBS, zymosan particles preincubated with human serum for 30 min at 37° C.) were dispensed to the appropriate wells by the luminometer. Chemiluminescence output from the wells was measured by the luminometer at 5-min. intervals for 30 min. Each test and control group was carried out using a minimum of triplicate samples, and negative controls without lucigenin or zymosan were included in the assays.

DETERMINATION OF NITRIC OXIDE PRODUCTION BY MACROPHAGES

Nitric acid production by macrophages was determined by the microplate method (A. H. Ding et al, "Release of reactive nitrogen intermediates and reactive oxygen intermediates from mouse peritoneal macrophages: Comparison of activating cytokines and evidence for independent production", 1988, *J. Immunol.* 141:2407–2412). Microplate wells were first seeded with $1 \times 10^5$ cells in RPMI-1640 media supplemented with 10% fetal bovine serum. After incubation for 48 hr at 37° C., 100 µl of the tissue culture supernates was transferred into wells of another microplate, an equal volume of Griess reagent (1% sulfanilamide, 0.1 T napthylethylene diamine dihydrochloride, 2.5% phosphate) was added to the wells, and the plate was incubated at room temperature for 10–60 minutes. The absorbance was then determined at 550 nm using a microplate reader (SLT Labinstruments, Austria). Nitric oxide production was determined at $NO_2^-$ using known amounts of sodium nitrite as standards.

CYTOKINE mRNA ISOLATION AND PCR AMPLIFICATION ISOLATION OF TOTAL RNA

For spleen and lung tissue samples, approximately 100–200 mg of freshly excised tissue was placed immediately in 2 ml of TRIzol™ reagent (phenol—guanidine isothiocyanate from BRL, Burlington, Ont.) in 15 ml polypropylene snapcap tubes. Samples were immediately homogenized for 60 sec at full power using a HandiShear homogenizer (VirTis, Gardiner, N.Y.) equipped with a 10 mm generator, and collected on ice. After homogenization, samples were aliquotted between two 1.7 ml nuclease-free siliconized microfuge tubes (Diamed, Mississauga, Ont.) Macrophage samples were taken by peritoneal lavage, followed by a washing of the cells in PBS. They were then pelleted and resuspended in 0.5 ml of TRIzol in 1.7 ml siliconized microfuge tubes. Samples were homogenized for 30 sec with a VirTis HandiShear homogenizer equipped with a 6 mm generator. An additional 0.5 ml of TRIzol was added to the macrophage samples, followed by gentle mixing. All samples were left up to an hour on ice, then 0.2 ml of chloroform was added per ml of TRIzol reagent used. The tubes were shaken vigorously by hand for 15 sec and then left 2–3 min at room temperature (RT). The samples were then pelleted at 12,000×g for 15 min at RT. The upper, aqueous phase was transferred to a 1.7 ml siliconized microfuge tube, being careful to avoid disturbing the interface region, and 0.5 ml of isopropanol was added. Samples were left 10 min at RT, and centrifuged at 12,000×g for 10 min at RT. The pellets were washed once with 80% ethanol (EtOH), drained well, and air dried 10–15 min in a fumehood. Samples were dissolved in 30 µl RNase-free dH20 (Promega, Madison, Wis.). Absorbance reading at 260/280 nm were performed on an aliquot and samples for the reverse transcriptase-polymerase chain reaction RT-PCR were adjusted to 1 µg/5 µl sample. Aliquots of RNA were also run on 0.8% formaldehyde-morpholinopropanesulfonic acid (MOPS) agarose gels run 3–4 hr at 100 V on ice with 1×MOPS running buffer (T. Maniatis et al, "Molecular Cloning: A Laboratory Manual", 1982, Cold Springs Harbor Laboratory, Cold Springs Harbor, N.Y.), and stained with ethidium bromide (EtBr) or Northern blotted to Hybond-N (Amersham, Oakville, ON). The Northern blot method is similar to the Southern blot method, except the gel was treated with several changes of sterile $dH_2O$, then 0.05 N NaOH for 30 min, followed by 0.1 M Tris-CH1 for 30 min and 2×SSC for 20 min before blotting.

REVERSE TRANSCRIPTASE-POLYMERASE CHAIN REACTION

The message amplification phenotyping (MAPPing) method (C. A. Brenner et al, "Message Amplification Phenotyping (MAPPing): A technique to simultaneously measure multiple mRNAs from small numbers of cells", 1989, *Biotechniques* 7:1096–1103, reviewed in J. W. Larrick, "Message amplification phenotyping (MAPPing): Principles, practice and potential", 1992 *Trends Biotechnol* 10:146–152) was used to assess the relative amounts of different cytokine mRNA transcripts. Aliquots of the RNA were converted to cDNA using a first-strand synthesis reaction (Clontech, Palo Alto, Calif.). Briefly, 1 µg of RNA and 20 pmol of oligo $(dT)_{18}$ in 12.5 µl $dH_2O$ was heated for 2 min at 65° C. and cooled on ice. The reaction mixture was adjusted to 1×reaction buffer [50 mM Tris-Hcl (pH 8.3), 75 mM KC1 and 3 mM $MgCl_2$], 1 mM of each dNTP, 1 U/µl RNase inhibitor and 10 U/µl M-MLV Reverse Transcriptase in a total volume of 20 µl. The reaction was incubated 1 hour at 42° C., followed by heating for 5 min at 94° C. to terminate the reaction. The reaction mix was diluted by the addition of 60 µl RNase-free water, and 6 µl was used in the polymerase chain reaction (PCR). Briefly 6 µl of diluted cDNA was added to 133 PCR buffer [10 mM Tris-HCl (pH 8.3), 50 mM KC1, 1.5 mM $MgCl_2$) and 0.01% (w/V) gelatin], 0.2 mM of each dNTPs, 0.4 mM 5' primer, 0.4 mM 3' primer and 2 U/reaction ampli-taq polymerase (Roche Molecular Systems, Branchburg, N.J.). Samples were run in oil-free PCR rubes (Bio/Can Scientific, Mississauga, Ont.) on a Perkin Elmer thermocycler. Thirty cycles were run using 1' at 94° C., 2' at 55° C. and 3 min at 72° C. After the final cycle, samples were held an additional 7 min at 72° C. Mouse cytokine primers and control template were purchased from Clontech (Palo Alto, Calif.) for interleukin 2 (I1-2), interferon gamma (IFN-γ), granuocyte macrophage colony stimulating factor (GM-CSF), tumor necrosis factor alpha (TNF-α) and actin. Control templates were run utilizing 20 pg of template. RT-PCR samples (10 μl) were analyzed on 1% TBE agarose gels run on BRL model H5 horizontal gel boats and visualized using EtBr.

SOUTHERN BLOT ANALYSIS

Control templates were isolated for use as probes as follows. Control template PCR reactions (50μ=7.5 μl gel loading buffer) were loaded onto 1% Tris-borate EDTA (TBE) Seaplaque low melting agarose (FMC Bioproducts, Rockland, Me.) gels, visualized with ethidium bromide, the band excised and extracted using phenol and chloroform (Wieslander, 1979). The DNA was EtOH precipitated, washed, dried and dissolved in 50 μl. An aliquot of 10 μl was labelled using the Multiprime random primer labelling system of Amersham (Oakville, Ont.). Briefly, the DNA was heated 2 min at 100° C. and cooled on ice. The reaction was adjusted to dATP, dGTP, TTP, 1×reaction buffer, random primer, 50 μCi α($^{32}$P)-dCTP (3000 Ci/mmol) (Amersham, Oakville, Ont.) and 8 & of Klenow fragment (Pharmacia, Baie d'Urfe, PQ) in a total volume of 50 μl. The reaction was incubated 30 min at 37° C., and 20 μl STE [100 mM naCl, 20 mM Tris-HC1 (pH u.5), 20 mM EDTA] was added. The sample was then loaded onto a pre-equilibrated Nu-trap™ column (Stratagene, La Jolla, Calif.) (pre-wet with 70 μl STE), and eluted with an additional 70 μl STE. The sample eluted (approximately 100 μl) was used to probe southern blots.

The southern blots were performed by equilibrating the TBE agarose gels (used to visualize the PCR products ) 30 min in 0.5 N NaOH, 30 min in 0.5 M Tris-HCl and 20 min in 2×SSC [0.3 M NaCl, 0.03 M sodium citrate (pH 7.0)] all at RT with gentle shaking. The DNA was transferred to Hybond-N membrane using a BRL Blot apparatus and blotting pads (BRL, Burlington, Ont.). Gels were blotted overnight utilizing 10×SSC. The membranes were air dried 5–10 min, UV fixed 5 min on a UV transluminator, and rehydrated in 2×SSC. The membranes were then prehybridized 2 hr in 50% Hood buffer [50% formamide, 5×SSC, 20 mM sodium phosphate (pH 6.7), 7% (w/v) sodium dodecyl sulphate, 1% (w/v) polyethylene glycol MW 20,000, 0.05% (w/v) nonfat powdered milk (Carnation)], and then hybridized overnight in 5 ml of 50% Hood buffer containing 2–5 ×10$^5$ cpm/ml [$^{32}$P]-labelled probe. Hybridizations were carried out in a Turbo-speed hybridization oven (Bio/Can Scientific, Mississauga, Ont.) in acrylic hybridization bottles. Samples were washed twice with 2×SSC, 1% SDS at RT and 20 min with 0.2×SSC, 0.1% SDS at 42° C. in hybridization bottles. This was followed by two washing with 0.2×SSC, 0.1% SDS at 42° C. in a Sci-era temperature controlled shaking water bath (Bellco Glass, NF). Membranes were exposed with Kodak XAR-5 X-ray film (Rochester, N.Y.) at −70° C.

BRIEF DESCRIPTION OF THE DRAWINGS

The results of the experiments described above are set out in the following with reference to the accompanying drawings, wherein.

DISCUSSION OF RESULTS

EFFECT OF CIPROFLOXACIN AND LIPOSOMAL CIPROFLOXACIN ON MACROPHAGE ACTIVATION

Figure 1:
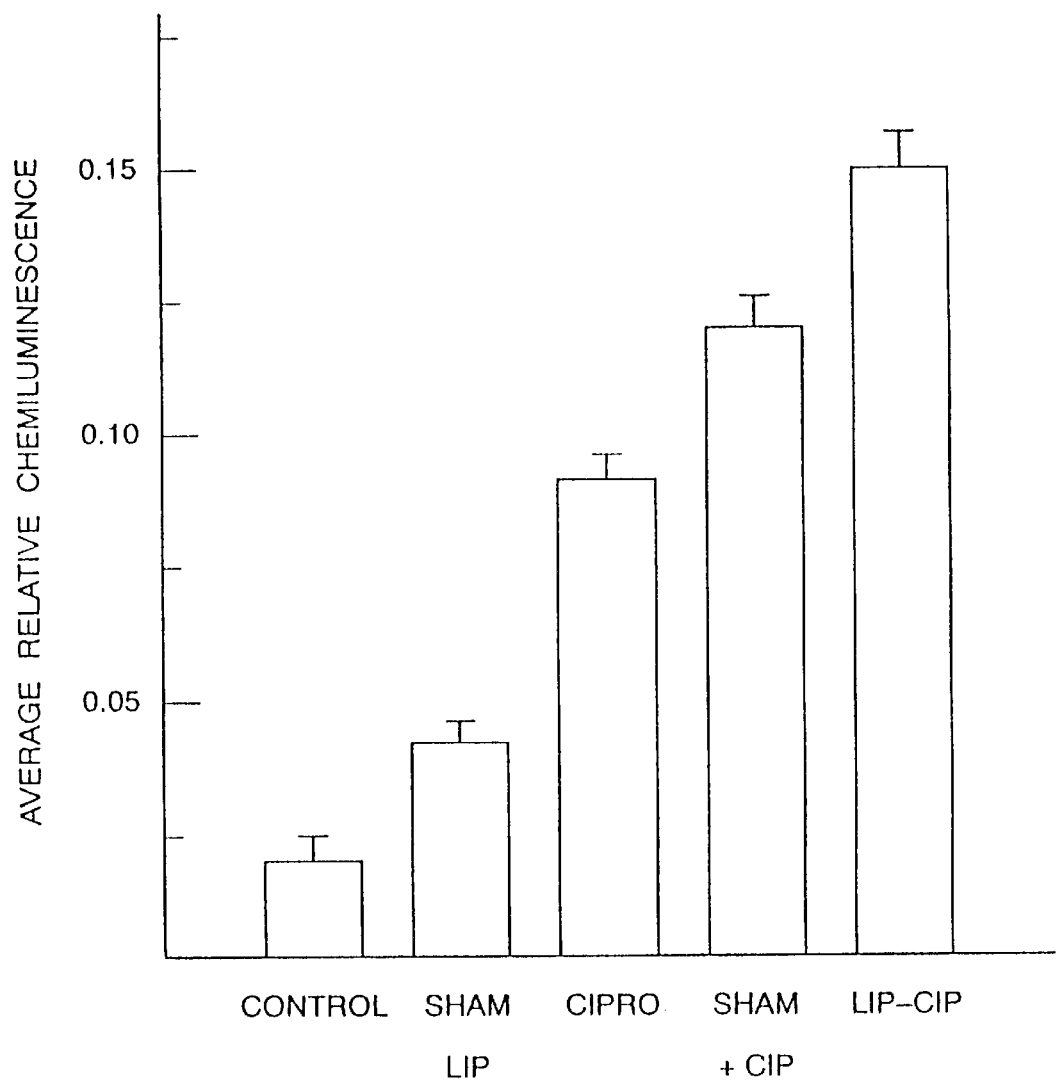
FIG. 1 is a bar graph of chemiluminescence for a variety of substances including the liposome-encapsulated ciprofloxacin of the present invention.
Figure 2:
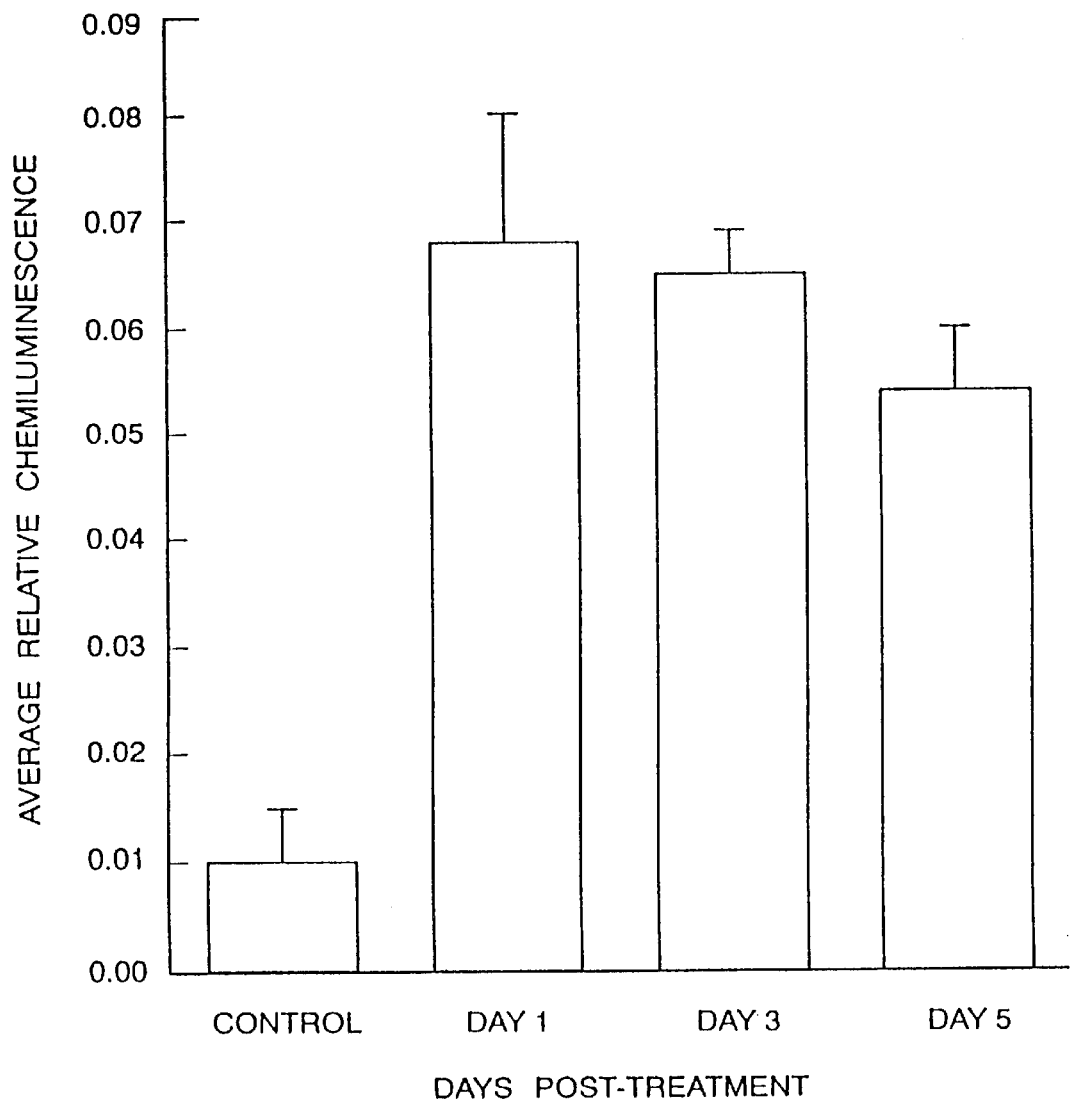
FIG. 2 is a bar graph of chemiluminescence versus time for liposome-encapsulated ciprofloxacin only.
Figure 3:
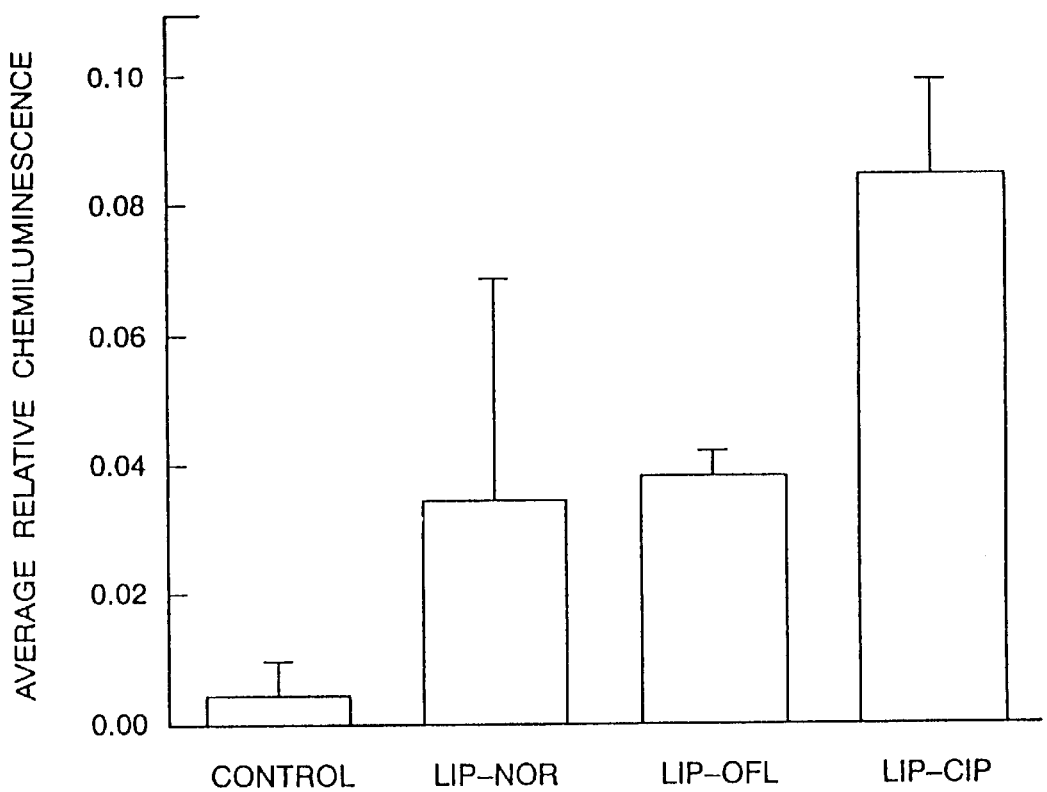
FIG. 3 is a bar graph of chemiluminescence for a variety of liposome-encapsulated antibiotics, including ciprofloxacin.
Figure 4:
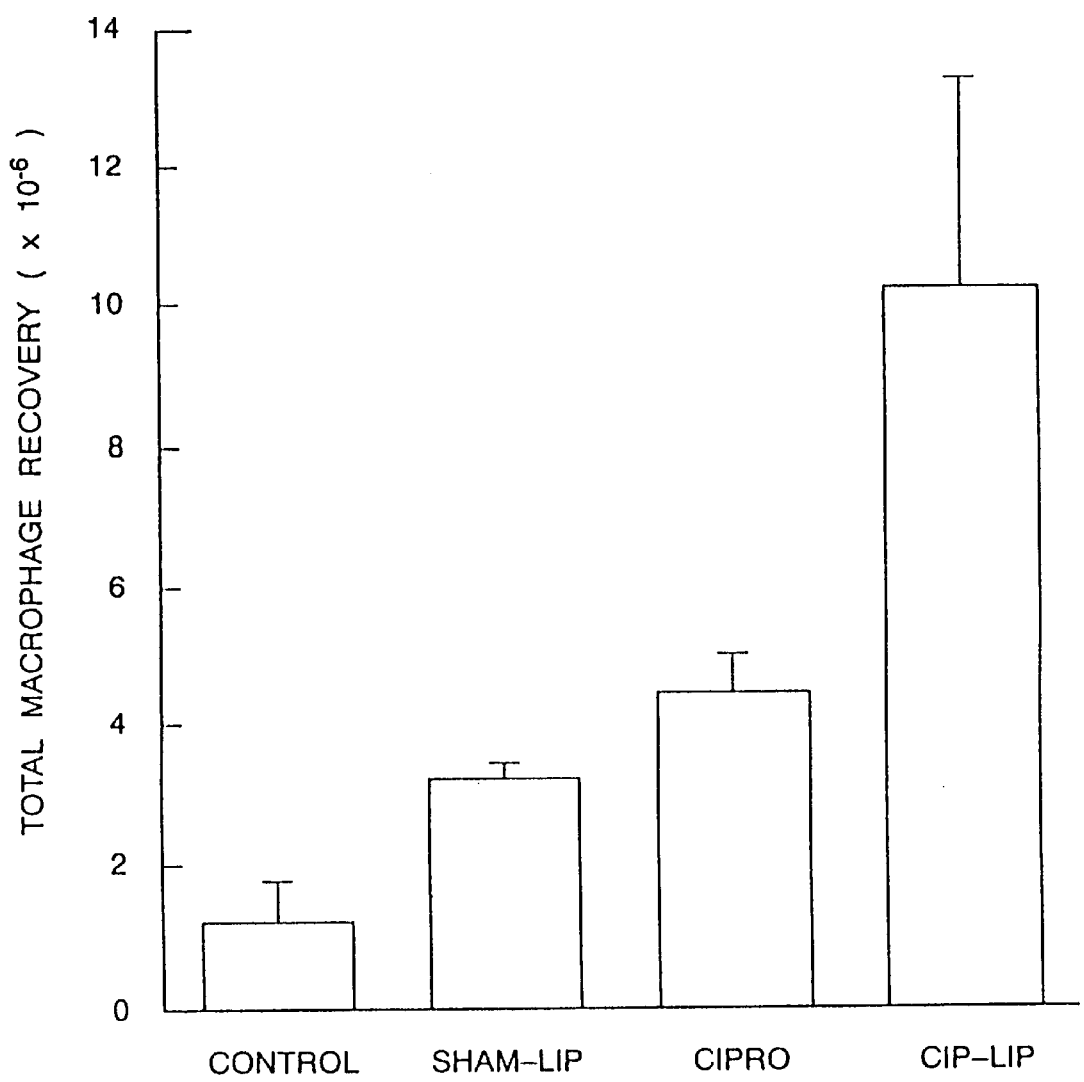
FIG. 4 is a bar graph of peritoneal macrophage yield for a variety of substances.

Chemiluminescence assays performed on peritoneal macrophages from mice treated with 3 daily administrations of ciprofloxacin, liposome-encapsulated ciprofloxacin, sham liposomes or PBS are shown in FIG. 1. The phagocytic activity of macrophages isolated from ciprofloxacin-treated mice with significantly enhanced and was found to be 4-fold higher than that from the untreated control mice. This increase in the phagocytic activity by ciprofloxacin was further enhanced by liposome-encapsulation with the phagocytic activity increased 7-fold over the untreated control group. Sham liposomes (without ciprofloxacin) did not cause a significant increase in the phagocytic activity. As shown in FIG. 2, the enhancement in the macrophage activation was sustained in duration and was 5-fold higher than untreated control group at day 5 post-administration. FIG. 3 illustrates that similar enhancement of macrophage activity of such magnitude was not observed with liposome-encapsulated ofloxacin of norfloxacin, the two other fluoroquinolones tested by the inventors. Moreover, as shown in FIG. 4, liposome-encapsulated ciprofloxacin was also found to cause in 5- to 10-fold increase in the peritoneal macrophage yield, compared to that of the untreated control mice. These results illustrate that ciprofloxacin is a potent macrophage activator as well as an effective chemotactic agent for macrophages, and that liposomes are an excellent drug delivery system for the potentiation of this effect.

EFFECT OF CIPROFLOXACIN AND LIPOSOME-ENCAPSULATED CIPROFLOXACIN ON NO PRODUCTION BY MACROPHAGES

Figure 5:
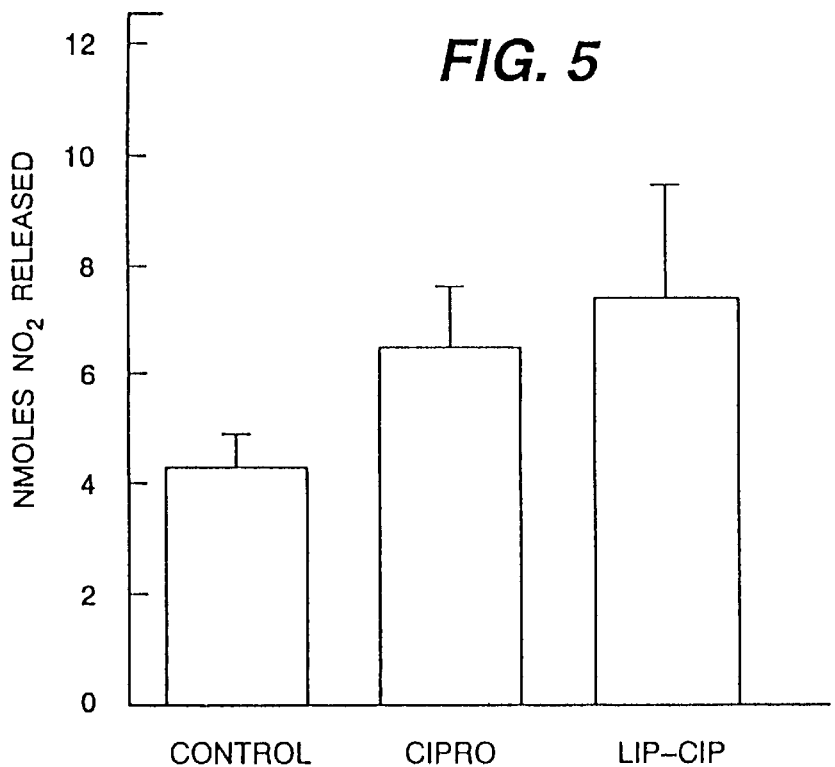
FIGS. 5 and 6 are bar graphs of released NO$_2^-$ for a variety of substances, including liposome-encapsulated ciprofloxacin.
Figure 6:
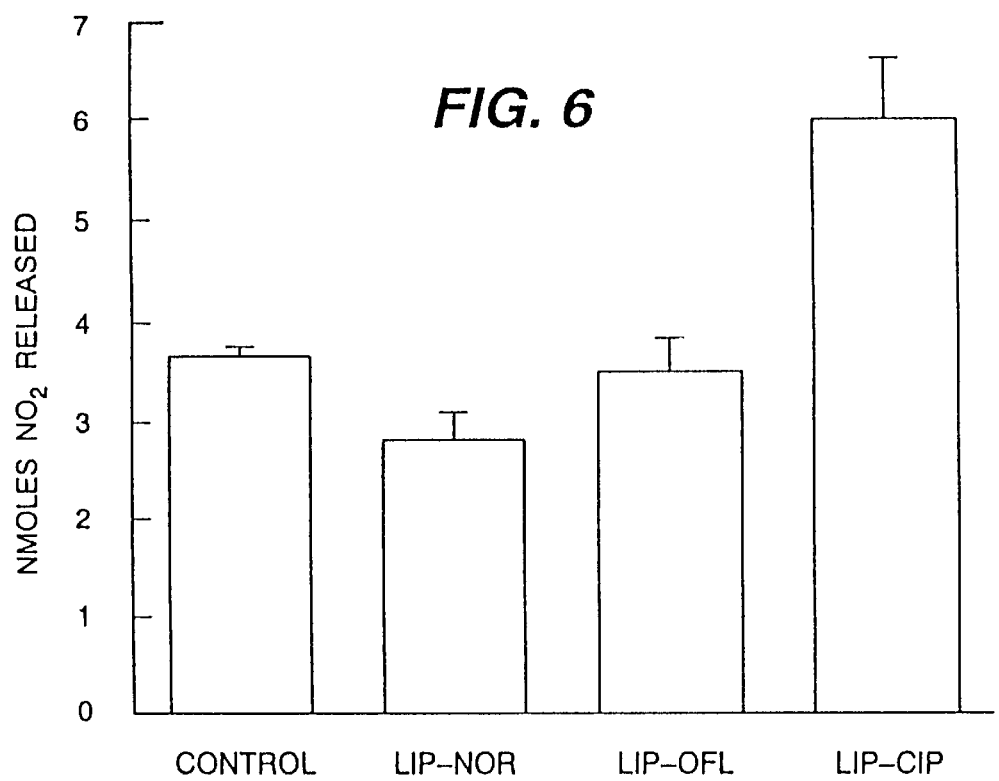

It is known that the production of NO is a mechanism by which activated macrophages kill invading microorganisms or abnormal tumor cells (I. A. Flesch et al, "Mechanisms involved in mycobacterial growth inhibition by gamma interferon-activated bone marrow macrophages: role of reactive nitrogen intermediates", 1991, Infect. Immun. 59:3213–3218, and J. Park et al, "L-arginine-dependent killing of intracellular Ehrlichia risticii by macrophages treated with gamma interferon", 1992, Infect. Immun. 60: 3504–3508). To determine whether macrophages activated by ciprofloxacin and liposome-encapsulated ciprofloxacin produce elevated levels of NO, tissue culture supernatants, in which these macrophages were cultured, were assayed for NO as NO$_2^-$in solution. As shown in FIG. 5, the NO level produced by macrophages from mice treated with liposome-encapsulated ciprofloxacin showed a significant 85%–95% increase compared to the level produced by untreated control macrophages (p<0.01). This increase in macrophage production of NO was also observed in ciprofloxacin-treated mice, but the level was significantly lower than the NO level produced by macrophages from mice treated with liposome-encapsulated ciprofloxacin (p<0.01). No increase in NO production was observed in macrophages from mice treated with liposome-encapsulated ofloxacin or norfloxacin (FIG. 6). The results show that liposome-encapsulated ciprofloxacin results in hyperproduction by NO by activated macrophages.

POLYMERASE CHAIN REACTION AND QUANTITATION OF CYTOKINE mRNA LEVELS

In addition to its ability to activate macrophage functions, liposome-encapsulated ciprofloxacin administered into the body are shown to enhance the de novo synthesis and production of interferon gamma (IFN-γ), and tumor necrosis factor alpha (TNF-α). Analysis by the inventors using reverse transcriptase-polymerase chain reaction (RT-PCR) and southern blots indicated that cellular levels of mRNA for these cytokines are significantly enhanced by liposome-encapsulated ciprofloxacin. Macrophages isolated from mice treated with liposomal ciprofloxacin showed enhanced mRNA levels for IFN-γ), and tumor necrosis factor alpha (TNF-α). It appears that both of the cytokines are produced by activated macrophages and sensitized T-lymphocytes, and are likely to be secreted at sites of inflammation, infections, and at tumor sites. Control action primers did not show any difference in the level of PCR amplification between liposome-encapsulated ciprofloxacin and untreated control group. Also, total RNA content within tissue groups showed not significant difference between liposome-encapsulated ciprofloxacin treated group and untreated group (data not shown).

SUMMARY

Ciprofloxacin is a fluoroquinolone antibiotic with potent broad spectrum activity. The present inventors have shown that in addition to its direct inhibitory effect on the bacterial gyrase system, ciprofloxacin, particularly when encapsulated within liposomes, has significant effects on a host's cellular immune response. Of primary importance, is the ability of liposome-encapsulated ciprofloxacin to cause a sustained hyperstimulation of macrophage functions. Macrophages play a central role in orchestrating the host immune defences against infections and tumor growth. Therefore, activation of these cells by liposome-encapsulated ciprofloxacin will provide a broad-spectrum, non-specific cellular immune response towards infections and killing of tumor cells.

The exact mechanism by which liposome-encapsulated ciprofloxacin stimulate macrophages is not entirely understood. Liposomes administered into the body are readily taken up and phagocytized by macrophages (I. J. Fidler et al, "Activation of tumoricidal properties in macrophages by liposome-encapsulated lymphokines: In vivo studies", 1980, *Liposomes and immunobiology*, B. H. Tom, and H. R. Six (eds.), Elsevier, Amsterdam, Holland, pp.109–118 and J. P. Wong et al, "Liposome potentiation of humoral immune response to lipopolysaccharide and 0-polysaccharide antigens of *Brucella abortus*", 1992, *Immunology* 77:123–128). The natural delivery of liposome-encapsulated ciprofloxacin to macrophages can result in significant increase in the intracellular accumulation of the drug in macrophages. Ciprofloxacin accumulated inside macrophages may penetrate the nuclear membrane and may bind directly with chromosomal DNA. Such binding between ciprofloxacin and DNA has been reported by others (S. Bazile et al, "Relationship between activity of sparfloxacin and other quinolones on DNA gyrase and their $Mg^{2+}$ mediated binding to DNA", 1993, 33rd *Interscience Conference on antimicrobial agents and chemotherapy*, Abstr. 1099, New Orleans.) may account for the increases in IFN-γ and TNF-α mRNA levels in mice treated with liposome-encapsulated ciprofloxacin. Produced mainly by activated macrophages, TNF-α plays a critical role in the normal host resistance to infections and to the growth of malignant tumors, acting as an immunostimulant and mediator of the inflammatory response (L. J. Old, "Tumor necrosis factor", 1988, *Sci. Am.* 258:59–60,69–75). IFN-γ is an effective inhibitor of viral replication and regulator of many immunological functions, and is known to enhance the macrophage-mediated killing of intracellular parasites (C. A. Nacy et al, "Macrophages, cytokines and leishmania", *Mononuclear phagocytes in cell biology*, G. Lopez-Berestein and J. Klostergaard (eds.), CRC Press, Boca Raton, Fla. pp 177–214). The ability of liposome-encapsulated ciprofloxacin to cause increases in the endogenous levels of these cytokines is indicative of its potential as an effective broad-spectrum immunostimulant.

The activation of macrophages in response to treatment with liposome-encapsulated ciprofloxacin could likely be an important contributing factor in the increase of NO production in these macrophages. Nitric oxide (NO) is an effective molecule that is produced by many cell types in the body. In macrophages, NO release from these cells acts as a cytotoxic molecule for the killing of invading microorganisms, intracellular pathogens and tumor cells (J. Park et al, "L-arginine-dependent killing of intracellular *Ehrlichia risticci* by macrophages treated with gamma interferon", 1992, *Infect. Immun.* 60:3504–3508, I. A. Flesch et al, "Mechanisms involved in mycobacterial growth inhibition by gamma interferon-activated bone marrow macrophages: role of reactive nitrogen intermediates", 1991, *Infect. Immun.* 59:3213–3218 and J. C. Drapier et al, "Differentiation of murine macrophages to express nonspecific cytotoxicity for tumor cells results in L-arginine-dependent inhibition of mitochondrial iron-sulfur enzymes in the macrophage effector cells", 1988, *J. Immunol.* 140:2829–2838). Because of NO's microbicidal and tumoricidal activities, several approaches have been employed to activate these macrophages to produce NO. These approaches, including use of bacterial lipo-polysaccharide (LPS), muramyl dipeptide, Staphylococcal exotoxin, toxic shock syndrome toxin, and specific cytokines like IFN-γ can result in significant increases in NO production by macrophages (D. J. Fast et al, "Staphylococcal exotoxins stimulate nitric oxide-dependent murine macrophage tumoricidal activity", 1991, *Infect. Immun.* 59:2987–2993, R. G. Kilbourne et al, "Endothelias cell production of nitrogen oxides in response to interferon-γ in combination with tumor necrosis factor, interleukin-1, or endotoxin", 1990, *J. Natl. Cancer Inst.* 82:772–776, A. H. Ding et al, "Release of reactive nitrogen intermediates and reactive oxygen intermediates from mouse peritoneal macrophages: Comparison of activating cytokines and evidence for independent production", 1988, *J. Immunol.* 141:2407–2412 and X. Zhang et al, "Necessity and sufficiency of beta interferon for nitric oxide production in mouse peritoneal macrophages", 1994, *Infect. Immun.* 62:33–40). However, these compounds themselves are extremely toxic, may cause endotoxic shock, and are not safe for human administration. The inventors have found that NO production by macrophages could be effectively enhanced by the administration of liposome-encapsulated ciprofloxacin. NO production from mice treated with liposome-encapsulated ciprofloxacin increased more than 100%–300% more than the level from untreated mice. This significant induction of NO production in activated macrophages could be a result of rise in the levels of host cell-derived cytokines. Indeed, IFN-γ and TNF-α have been recently shown to act together to induce NO production in vitro in thioglycolate-elicited macrophages (X. Zhang et al, "Necessity and sufficiency of beta interferon for nitric oxide production in mouse peritoneal macrophages", 1994, *Infect. Immun.* 62:33–40). Since the results set out hereinbefore show that both of these cytokines are induced by liposome-encapsulated ciprofloxacin, it is reasonable to speculate that the induction of NO production may be unregulated by the levels of these cytokines.

In summary, the ability of liposome-encapsulated ciprofloxacin to dramatically enhance macrophage functions, induce NO production, and augment the production of cytokines render it a novel immunoprophylactic and immunotherapeutic agent with unique clinical potential. Liposome-encapsulated ciprofloxacin and other quinolones could be extremely useful in antimicrobial, anticancer and in AIDS therapies. In these cases, the immunological status of these patients is often compromised or suppressed, making them susceptible to microbial infections and to the development of tumor growth. Selective augmentation of cellular immunity by activation of the microbicidal and tumoricidal activities of macrophages, induction of NO and cytokine productions, could be of primary importance to these individuals, in terms of protecting them against microbial infections and inducing their cellular host defence to tumor cells.

The embodiments of the invention in which an exclusive property or privilege is claimed are defined as follows:

1. A method of enhancing nitrogen oxide in macrophages of an animal to thereby enhance the phagocytic activity of said macrophages said method comprising administering to said animal an effective amount of ciprofloxacin encapsulated in liposomes.

2. A method of increasing the cellular levels of interferon gamma, tumor necrosis factor-alpha or both to thereby increase the phagocytic activity of macrophages in an animal, said method comprising administering to said animal an effective amount of ciprofloxacin encapsulated in liposomes.

* * * * *